(12) United States Patent
ter Horst et al.

(10) Patent No.: US 9,546,942 B2
(45) Date of Patent: Jan. 17, 2017

(54) SYSTEM AND METHOD FOR OPTIMIZING SELECTION OF AN AIR FILTER

(75) Inventors: Dirk ter Horst, Boca Raton, FL (US); Hans-Joachim Lippold, Lake Worth, FL (US)

(73) Assignee: LPD Technologies, Inc., Deerfield Beach, FL (US)

(*) Notice: Subject to any disclaimer, the term of this patent is extended or adjusted under 35 U.S.C. 154(b) by 879 days.

(21) Appl. No.: 13/806,224

(22) PCT Filed: Jun. 24, 2011

(86) PCT No.: PCT/US2011/041907
§ 371 (c)(1),
(2), (4) Date: Dec. 21, 2012

(87) PCT Pub. No.: WO2011/163638
PCT Pub. Date: Dec. 29, 2011

(65) Prior Publication Data
US 2013/0103352 A1    Apr. 25, 2013

Related U.S. Application Data

(60) Provisional application No. 61/358,208, filed on Jun. 24, 2010.

(51) Int. Cl.
*G01N 15/08* (2006.01)
*B01D 46/42* (2006.01)

(52) U.S. Cl.
CPC ........... *G01N 15/0826* (2013.01); *B01D 46/42* (2013.01)

(58) Field of Classification Search
CPC .................................................. G01N 15/0826
USPC .......................................................... 702/182
See application file for complete search history.

(56) References Cited

U.S. PATENT DOCUMENTS

| | | | | |
|---|---|---|---|---|
| 4,751,501 A * | 6/1988 | Gut | ........................ | B01D 46/46 340/607 |
| 6,009,404 A * | 12/1999 | Eimer | .................. | B01D 29/117 210/106 |
| 6,453,257 B1 * | 9/2002 | Juhasz | .................... | B01D 46/44 702/114 |
| 2010/0017151 A1 * | 1/2010 | Kerrigan | ............ | B01D 46/0086 702/47 |

OTHER PUBLICATIONS

International Search report dated Nov. 22, 2011.

* cited by examiner

*Primary Examiner* — Gregory J Toatley
*Assistant Examiner* — Yoshihisa Ishizuka
(74) *Attorney, Agent, or Firm* — Bachman & LaPointe, PC

(57) ABSTRACT

A method for estimating energy use in an air filtration system using a preselected air filter includes the steps of: entering filtration system information into a computer having access to dust holding capacity—pressure drop curves for a plurality of air filters; determining an estimated current energy use of the air filtration system for a current air filter in the system; and presenting the estimated energy use on a display of the computer. Proposed filters can be evaluated and filter operation and changing cycle can be optimized.

10 Claims, 14 Drawing Sheets

| | America's Center | | | |
|---|---|---|---|---|
| Bill Smith | bsmith@americacenter.org | | 314-342-5021 | LPD |
| 701 Convention Plaza, St. Louis MO, 63101 | | | | |

| Summary estimate | Riga-Flo | Legacy with SAME Change-out cycle | Legacy with OPTIMAL time between filter changes |
|---|---|---|---|
| Filter Manufacturer | Camil Farr | CLC | CLC |
| Average time between filter changes | 12.00 months | 12.00 months | 9.61 months |
| Average pressure drop of filters when changed | 1.50 inch w.g. | 1.08 inch w.g. | 0.85 inch w.g. |
| Number of filter changes | 1.00 per year | 1.00 per year | 1.25 per year |
| Annual energy consumption | 1,114,273.48 kWh | 875,788.22 kWh | 774,064.27 kWh |
| Annual energy cost | $111,427.35 | $87,578.82 | $77,406.43 |
| Total annual filtration cost | $134,407.35 | $116,303.82 | $113,283.33 |
| Total annual filtration cost savings | | $18,103.53 13.47% | $21,124.02 15.72% |
| Annual CO2 emission | 1,468,857.59 lb | 1,154,481.55 lb | 1,020,387.01 lb |
| Annual CO2 emission savings | | 314,376.04 lb 21.40% | 448,470.58 lb 30.53% |

Current filter vs proposed with same operating time ☒

Current filter vs proposed with optimized operating time ☒

Comments / notes

DISCLAIMER

FIG. 5a

| | America's Center | | |
|---|---|---|---|
| Bill Smith | bsmith@americacenter.org | 314-342-5021 | LPD |
| 701 Convention Plaza, St. Louis MO, 63101 | | | |

| Estimate details | Riga-Flo | Legacy with SAME Change-out cycle | | Legacy with OPTIMAL time between filter changes | |
|---|---|---|---|---|---|
| Filter Manufacturer | Camil Farr | CLC | | CLC | |
| MERV rating | 14.00 | 14 | | 14 | |
| Nominal size | 24" x 24" x 12" | 24" x 24" x 12" | | 24" x 24" x 12" | |
| Filter part number | | | | | |
| Filter type | Cartridge | Cartridge | | Cartridge | |
| Number of filters per set | 383U | 383U | | 383U | |
| Purchase cost of complete filter set | $22,980.00 | $28,725.00 | | $28,725.00 | |
| Incineratable | no | yes | | yes | |
| UL900 compliant | no | yes | | yes | |
| Average time between filter changes | 12.00 months | 12.00 months | | 9.61 months | |
| Average press. drop of filters when changed | 1.50 inch w.g. | 1.08 inch w.g. | | 0.85 inch w.g. | |
| | Per cycle / Per year | Per cycle | Per year | Per cycle | Per year |
| Cost of filter set | $22,980.00 / $22,980.00 | $28,725.00 | $28,725.00 | $28,725.00 | $35,876.90 |
| Energy consumption per filter set | 1,114,273.48 KWh / 1,114,273.48 KWh | 875,788.22 KWh | 875,788.22 KWh | 619,758.05 KWh | 774,064.27 KWh |
| Energy cost per filter set | $111,427.35 / $111,427.35 | $87,578.82 | $87,578.82 | $61,975.81 | $77,406.43 |
| Labor cost to change out filter set | $0.00 / $0.00 | $0.00 | $0.00 | $0.00 | $0.00 |
| Disposal cost of filter set | $0.00 / $0.00 | $0.00 | $0.00 | $0.00 | $0.00 |
| Freight cost for filter set when acquired | $0.00 / $0.00 | $0.00 | $0.00 | $0.00 | $0.00 |
| Administrative cost to purchase filter set | $0.00 / $0.00 | $0.00 | $0.00 | $0.00 | $0.00 |
| Other cost per cycle | | | | | |
| Other cost per year | | | | | |
| Total filtration Cost | $134,407.35 / $134,407.3 | $116,292.67 | $116,303.82 | $90,700.81 | $113,283.33 |
| $CO_2$ emission | 1,468,857.59 lb / 1,468,857.59 lb | 1,154,370.83 lb | 1,154,481.55 lb | 816,977.46 lb | 1,020,387.01 lb |

Comments / notes
1. Calculations of estimates based on attached independent test report at 2000 cfm: BH-09-1182, legacy12-9.5

FIG. 5b

| America's Center | | | |
|---|---|---|---|
| Bill Smith | bsmith@americacenter.org | 314-342-5021 | LPD |
| 701 Convention Plaza, St. Louis MO, 63101 | | | |

| CUSTOMER FILTRATION SYSTEM | | | Current Filter | |
|---|---|---|---|---|
| System operates | | Filter name | Riga-Flow | |
| month/year | 12 | Manufacturer | http://lpdedikon.eniac.com/ | |
| days/month | 30 | MERV rating | 14 | |
| hours/day | 24 | Nominal size | 24" x 24" x 12" | inch |
| Average change-out cycle | 12.00 months | Part number | 096966004 | |
| Number of filters in system | 383 | Filter type | Rigid Box | |
| Efficiencies of | | Incinerable | no | |
| Motor | 86 % | UL900 compliant | yes | |
| Drive | 99 % | Average Pressure drop of filter when changed | 1.50 | inch W.G. |
| Fan | 68 % | Cost of each filter | $ 60.00 | |
| Local CO2 emission (per code) | 1.318 lb / kWh | Additional cost | | |
| Local Energy cost | 0.10 $ / kWh | Labor cost to change out complete filter set | $ 0.00 | |
| System has variable air flow | yes | Freight cost for filter set at time of acquisition | $ 0.00 | |
| Fan blades are | | Disposal cost of filter set | $ 0.00 | |
| Forward inclined | yes | Administrative cost to purchase filter set | $ 0.00 | |
| Backward inclined | no | Other cost per cycle | | |
| Radial | no | | $ | |
| Other | | | $ | |
| Comments / notes | | | $ | |
| | | Other cost per year | | |
| | | | $ | |
| | | | $ | |
| | | | $ | |

PREMISES

FIG. 5c

- The unfiltered air composition and the atmospheric conditions at the customers site and to which the filters are exposed to remain constant during the analyzed and projected period.
- The customer operates his air filtration system identically every year (air volume, hours per day, per month and per year) during the analyzed and projected period.
- The unit costs of air filters, energy and all other associated unit costs remain equal during the analyzed and projected period.
- Any filter of equal efficiency, size and air flow as the filter that the customer uses will operate the equal amount of time at the same ASHRAE Dust loading point
- The filtration cost calculation is based on the customers filtration experience at the specific site, the reports of ASHRAE 52.2 independently tested filters, the cost of energy and all other associated costs that are shown on the report.
- The calculation of maximum filter change-out times does not take into account filter change-outs due to mold smell or customer convenience.
- The ASHRAE 52.2 test standard is a valid standard for comparing air filter performance.
- The filters being evaluated operate in a variable air volume system. If the system does not have variable air volume capability, the energy savings will only be realized if the fan has radial or backward leaning blades.

FIG. 5d

COMPANY AND CONTACT INFORMATION

Case ID: 123

| | | | | | |
|---|---|---|---|---|---|
| Company Name: | AAF | | | | |
| Contact Name: | Bill Barrows | Email: | xxxxxxxxxxxxxx@XXXXXXXXX.com | Phone: | 5555555 |
| Address: | Louisville, KY | | | Zip Code: | |

CUSTOMER FILTRATION SYSTEM

| | | | | | | |
|---|---|---|---|---|---|---|
| Local CO2 emission (per code): | 1.31822 | lb/kWh Local Energy cost: | 0.12 | $/kWh System has variable air flow: | ○ Yes | ⦿ No |
| click here to view map | | cfm Current total air flow: | 24000 | cfm Customer designation: | HVAC | |
| Air Flow per filter: | 2000 | Fan blades are | | Comments: | | |
| Industry Type: | Commercial | Forward inclined | ⦿ Yes ○ No | | | |
| | | Backward inclined | ○ Yes ⦿ No | | | |
| | | Radial | ○ Yes ⦿ No | | | |

FIRST STAGE    Second Stage    Weather Louver

CUSTOMER FILTRATION SYSTEM

| | | | CURRENT FILTER | PROPOSED FILTER |
|---|---|---|---|---|
| System Operates | | Filter Name: | Varicel II AAF M14 4" B G AAF | Geopleat FGI M14 4" 5.5m2 B S FGI |
| Months per year: | 12 | | | Geopleat 5.5 |
| Days per month: | 30 * | Manufacturer: | AAF | FGI |
| Days per month: | 24 * | MERV rating: | 14 | |
| Average change-out cycle: | 3 * month | Nominal Size Width x Height x Depth | 24 " x 24 " x 4 " | 24" x 24" x 4" |
| | | Part Number: | | |
| Number of filters in system: | 12 * filters | Filter Type: | | Cartridge |
| Efficiency of Motor: | 86 * % | Frame Type: | Box | Box |
| | | Incinerable: | ⦿ Yes ○ No | No |
| | | U_900 compliant: | ○ Yes ⦿ No | No |
| Drive: | 99 * % | Average Pressure drop of filter when changed: | 1.5 inch W.G. | |
| Fan: | 68 * % | Cost of each filter: | $ 42 * | $ 45 * |
| | | Additional cost | | |
| | | Labor cost to change out complete filter set: | $ 0 | $ 0 |
| | | Freight cost of filter set at time of acquisition: | $ 0 | $ 0 |
| | | Disposal cost of filter set: | $ 0 | $ 0 |
| | | Administrative cost to purchase filter set: | $ 0 | $ 0 |
| | | Other costs per cycle: | | |
| | | Description: Cost: | $ | $ |
| | | Description: Cost: | $ | $ |
| | | Description: Cost: | $ | $ |
| | | Other Yearly costs: | | |
| | | Description: Cost: | $ | $ |
| | | Description: Cost: | $ | $ |
| | | Description: Cost: | $ | $ |

FIG. 8

Copyright 2008. Venezuela. Developed by Eniac

COMPANY AND CONTACT INFORMATION                                              Case ID: 123

Company Name: AAF
Contact Name: Bill Barrows     Email: xxxxxxxxxxxxxx@XXXXXXXXX.com    Phone: 5555555
Address: Louisville, KY                                                Zip Code:

CUSTOMER FILTRATION SYSTEM

Local CO2 emission (per ccde): 1.31822 lb/kWh    Local Energy cost: 0.12 $/kWh    System has variable air flow:  ○ Yes  ⊙ No
click here to view map    cfm   Current total air flow: 24000 cfm   Customer designation: HVAC
Air Flow per filter: 2000                Fan blades are
Industry Type: Commercial                 Forward inclined   ⊙ Yes  ○ No    Comments:
                                          Backward inclined  ○ Yes  ⊙ No
                                          Radial             ○ Yes  ⊙ No FIRST STAGE   Second Stage   Weather Louver

CUSTOMER FILTRATION SYSTEM                         CURRENT FILTER              PROPOSED FILTER

System Operates                      Filter Name:    Varicel M-Pak A A F m14 6" H G BH    Titan FGI M14 12" H G CLC Months per year:  12                                                                      Titan
Days per month:   30 *               Manufacturer:                                        FGI
Days per month:   24 *               MERV rating:
                                     Nominal Size Width x Height x     24 " x 24 " x 6 "  24" x 24" x 12"
Average change-out cycle: 12 * month Depth
                                     Part Number:
Number of filters in system: 12 * filters   Filter Type:                                  Cartridge
Efficiency of                        Frame Type:     Header                               Header
  Motor:         86 *  %             Incinerable:    ○ Yes  ⊙ No                          No
                                     UL 900 compliant: ○ Yes  ⊙ No                        No
Drive:            99 *  %
                                     Average Pressure crop of filter   1.0  inch W.G.
                                     when changed:
Fan:              68 *  %            Cost of each filter:              $ 65 *            $ 60 *
                                     Additional cost
                                     Labor cost to change out         $ 0                $ 0
                                     complete filter set:
                                     Freight cost of filter set at time $ 0              $ 0
                                     of acquisition:
                                     Disposal cost of filter set:     $ 0                $ 0
                                     Administrative cost to purchase  $ 0                $ 0
                                     filter set:
                                     Other costs per cycle:
                                     Description:                    $                   $
                                     Cost:
                                     Description:                    $                   $
                                     Cost:
                                     Description:                    $                   $
                                     Cost:
                                     Other Yearly costs:
                                     Description:                    $                   $
                                     Cost:
                                     Description:                    $                   $
                                     Cost:
                                     Description:                    $                   $
                                     Cost:

FIG. 9

Copyright 2008. Venezuela. Developed by Eniac

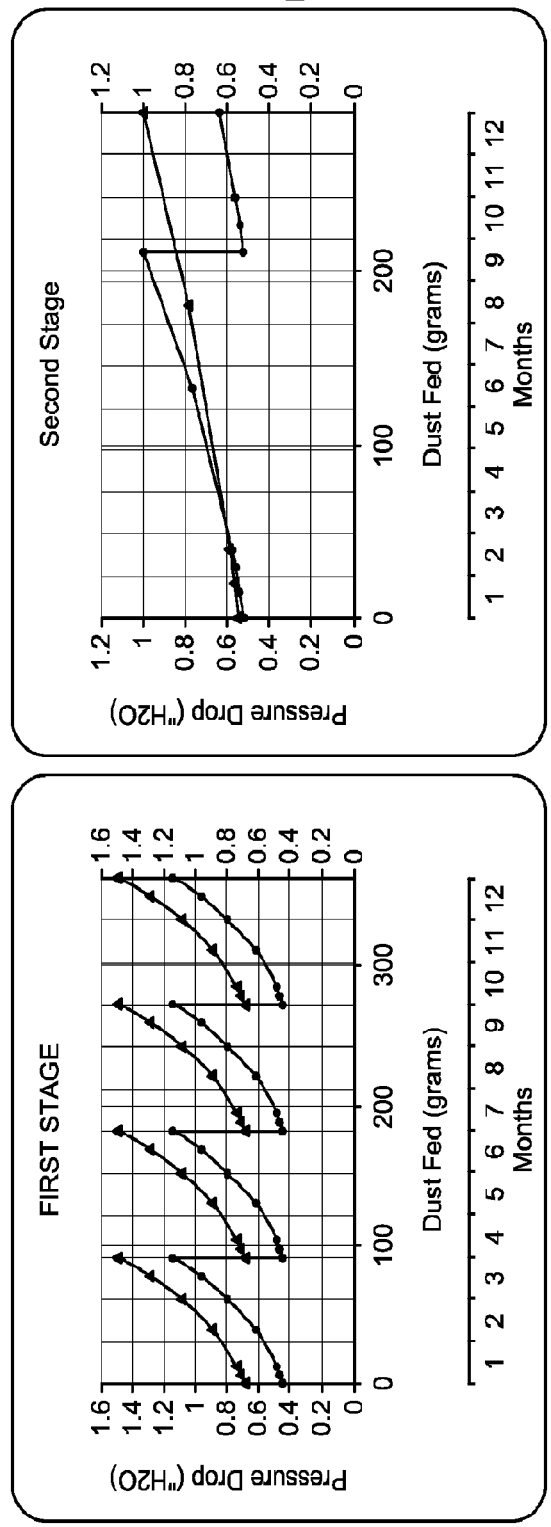

SYSTEM AND METHOD FOR OPTIMIZING SELECTION OF AN AIR FILTER

CROSS REFERENCE TO RELATED APPLICATIONS

This application is a non-provisional application which claims priority to U.S. provisional application Ser. No. 61/358,208 filed Jun. 24, 2010.

BACKGROUND OF THE INVENTION

A portion of the disclosure of the patent document contains material which is subject to copyright protection. The copyright owner has no objection to the facsimile reproduction by anyone of the patent document or the patent disclosure, as it appears in the Patent and Trademark Office patent file or record, but otherwise reserves all copyright rights whatsoever.

The invention relates to a system and method for improving the selection and operation of filters of an HVAC system and other air/gas filtration systems.

Air handling systems such as any of a wide variety of HVAC systems typically utilize various air handling and conditioning equipment and ducts and the like for transporting air from one location to another and conditioning that air as it is being transported prior to introduction of the conditioned air into the space to be conditioned.

It is frequently desirable to filter the air in the course of this handling, for the purposes of removing various particulate and/or gaseous matter and the like which may be entrained in the air, and thereby provide a better quality conditioned air to the conditioned space. As can be appreciated, filters in such systems gradually accumulate such entrained particulate and other matter from the air, and as this matter accumulates on the filter, the resistance to flow of air through the filter increases. This leads to an increase in pressure drop at the filter, and thus a decrease in operating efficiency.

Due to these factors, there is a need to change filters in air conditioning systems on a periodic basis. This changing of filters can be as simple as opening of one or more filter housings in an easy to access location and installing a new filter, to replacing potentially large filters in difficult to reach locations in industrial facilities. Regardless of the environment, the best time for changing such filters, and for that matter the best type of filters to use, is often a matter of guesswork.

Based on the above, much efficiency is lost through utilization of a filter that is not best suited due to the cost of the energy and other filtration associated costs that are associated to the particular filter during its useful life, and also through changing such filters either too early or too late. The need exists for an improved approach to reduce losses due to inefficiency of the filter and guesswork decisions upon when a filter should be changed.

The present invention is intended to meet that need.

SUMMARY OF THE INVENTION

In accordance with the invention, a system and method are provided for enhancing the economic efficiency and operation of HVAC and other filtration systems by identifying and utilizing more energy and cost efficient filters for a particular system, adjusted to the filter user's real location and experience and for identifying the most advantageous time for replacing such filters. The system takes into account the theoretical energy consumption of the air filter over its entire lifetime, as well as one or more additional factors which lead to cost of running an air filter such as the cost of the energy consumed by operating the system with the particular air filter in place, cost directly or indirectly related to filtration such as the cost of the filter, the cost of changing the filter, the cost of disposing of filters, loss of production during filter change-out, cost resulting from the purchasing of the filters, and the like, and finally costs which are not directly or indirectly related to the air filtration itself, but rather are peripherally related costs, such as the cost of storing a supply of filters, carbon footprint costs or benefits, and the like.

In addition, the system can determine the carbon footprint of the used and proposed filters to help the filter user to select a more environmentally friendly filter. Further, if at some point the carbon footprint leads to an additional economic cost, the system can be communicated with a source of that cost and this factor can then be added to the factors used to determine the economic effect of using a particular filter.

The system also takes customer experience into account, factoring in what specific filters the filter user is using or has used and what the experience is or was with those filters. Useful experience information includes how often and at what pressure drop the filter or filters are normally changed by the user. Standard factors can also be used, and preferably these factors are the ASHRAE 52.2 and dust holding capacity vs pressure drop curves, and standard factors should be used consistently for all filters being evaluated. Other standards could also be used, such as EN771 or the like. Knowing filter manufacturer and model/type that is being used, the change-out time and the pressure drop at that change-out time as per user experience (or estimate of such experience), the ASHRAE DHC vs. delta P of that particular filter allows the system to indirectly determine air quality at the location and the estimates of economic performance with proposed filters. Further, the system can take numerous other factors into account to make the filter economic evaluation estimation as accurate to the specific user location as possible. Additional examples of cost information that can be taken into account include work or school absenteeism caused by inappropriate air filtration: use of a higher efficiency filter that consumes more energy but that produces cleaner air and in turn reduces the absenteeism in schools and improves the education efficiency can lower cost of teaching and providing a better education, and in a business can increase the overall productivity. Thus, a user of the system could enter estimates of this information as well.

When none, or only some of the experience information is available, various different typical numbers can be assumed, and cost information provided for each different value. For example, the industry's typical recommendation of changing at a pressure drop of 1.5" w.g. (water gauge) can be a starting point, and savings information by switching to a different filter can be determined and presented to a user of the system at 1.5" w.g. as well as 1.4" w.g., 1.3" w.g., etc.

By assembling the various components of information as desired by the person utilizing this process, factors which are important to a particular user can be accounted for in determining the benefits of changing to a different type of filter, and further can be utilized to determine the best lifespan for use of such filters in the system. This process can advantageously be utilized by building managers, sellers of filters, government officials and even household consumers, any of whom can benefit from the determination made according to the process. This program, system and method are intended to contribute to minimizing the total cost of air filtration. In some systems, multiple stage filters are used. In such systems, it is common for the earlier stage filters to need to be removed in order to access a later stage filter. For example, in order to access and change the third stage filter, it may be necessary to remove the second stage filter. In accordance with the invention, it is recognized that the most efficient way to change such filters is to change the third stage filter when the second stage filter is also due to be changed. Thus, the system according to the invention, when outputting a report of proposed filter use and changing schedule, will formulate the proposal so that the change out period for the third stage filter is equal to or a multiple of the change our period of the second stage.

According to the invention, a method is provided for estimating energy use in an air filtration system using a preselected air filter, comprising the steps of: entering filtration system information into a computer having access to dust holding capacity—pressure drop curves for a plurality of air filters; determining an estimated current energy use of the air filtration system for a current air filter in the system; and presenting the estimated energy use on a display of the computer.

In accordance with one preferred embodiment, the entered information can also include information related to a proposed air filter different from the current air filter, and an estimated energy use of the air filtration system using the proposed air filter is determined and presenting on the display of the computer.

BRIEF DESCRIPTION OF THE DRAWINGS

A detailed description of preferred embodiments of the present invention follows, with reference to the attached drawings, wherein:

FIGS. 2-5 show display screens which can be generated with the system and method of the invention;

FIGS. 8 and 9 shows information entry screens which can be generated with the system and method of the invention for systems with multiple stages; and FIGS. 10 and 11 show display screens which can be generated with the system and method of the invention showing output (cost savings and optimization) of the system for a proposed air filter for a multiple stage system.

DETAILED DESCRIPTION

The invention relates to a system and method for determining the estimated total costs for use of a particular air filter in an HVAC system. As will be discussed below, this allows the total cost of using various different types of filters to be estimated so that a decision can be made to use what may be the most cost effective filter for that particular system. The process of the invention involves evaluating a series of different factors to make the determination of the costs of operating a filter and then can further include an evaluation of a specific filter, for example, the most cost effective filter, to determine when it is most advisable to change that filter.

The system can be embodied in a series of programmed machine operations which can be carried out on a wide variety of computing devices such as desktop or laptop computers, PDAs, industrial workstations and/or servers which can be accessed by any of the foregoing. While it is anticipated that the machine instructions would be embodied in a program which is compatible with typical operating systems, it could also be incorporated into a dedicated machine which could have different operating systems as well, the key being to have programmed capability for accepting various choices from the user and storing various relationships to which the choices of the user are applied to determine certain output, and finally with formatting capabilities to present that data in a desired manner, for example in graph or chart form or the like.

Figure 1:
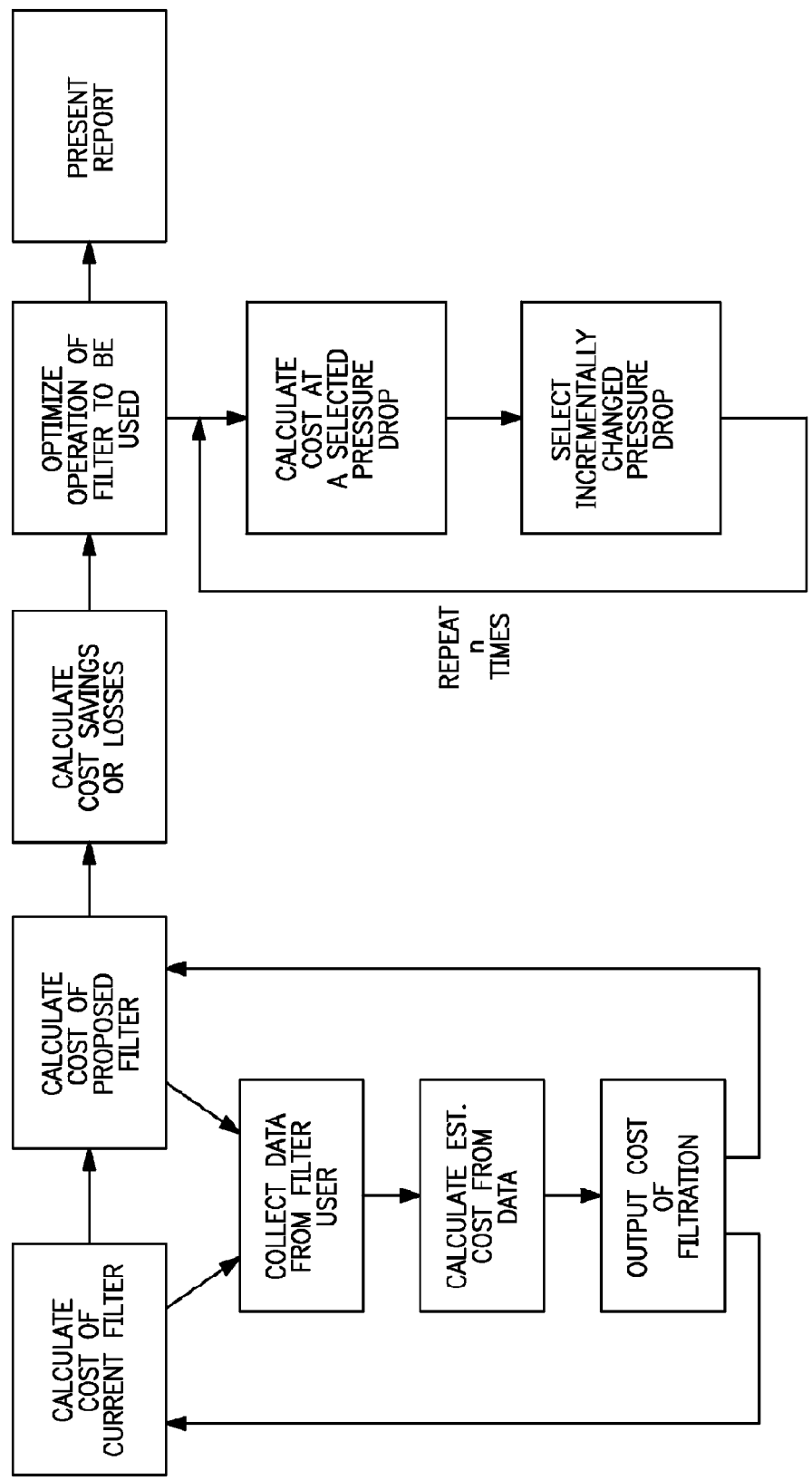
FIG. 1 is a flow chart showing operation of the system in accordance with the present invention.

FIG. 1 shows a schematic flowchart of various steps which can be taken by the process in accordance with the invention. The first step shown involves determining the theoretical energy consumption of the currently used air filter in question, that is, the filter that is being or has been used. This is based upon a determination of the energy consumption of the air filter when first installed, as well the energy consumption of the air filter just prior to it being changed out and the gradually increasing energy consumption of the air filter between these points. This relationship can most accurately be estimated by determining the change in pressure drop for a filter, which in turn can be estimated on the basis of, for example, utilizing ASHRAE test standard 52.1 or 52.2. The test curve generated by this standard represents the practical behavior of a particular filter in a standardized set up of test conditions. Due to different environmental factors, this curve is of course an estimate, and may not represent the actual behavior of the air filter. However, any error from this difference is minimized greatly due to the fact that the proposed filter evaluation is based upon its own ASHRAE test curve, and therefore the evaluation of both filters would have the same error, and the error would essentially cancel itself out, since the actual and proposed filters are being evaluated relative to each other.

The pressure drop of the air filter at the time that particular user changes out the air filter is either determined by the use of pressure drop gauges at the location, or if it is not possible to measure the pressure drop of the filters at the time of change out, the system and method can be run or otherwise carried out using different incremental pressure drop estimates at the time of change out in order to generate the corresponding economic estimate and optimized change out point. For example, it is typically recommended that filters be changed out when the pressure drop has reached approximately 1.5" w.g. Filter user experience, if different, is entered by the filter user and/or operator of the system or if it is not known, it is entered and the method carried out at 1.5", then at 1.4", then at 1.3" and so on in order to get an idea of the effect of different filters. In some areas, the industry maximum filter change out pressure drop standard, used as an estimate when needed, is different. For example, in Europe the industry standard for changing out filters is currently at a maximum of 1.8" w.g.

In connection with the above determination, the rate of change of the pressure drop from initial use through to change out of a filter can be used to generate a non-linear curve of pressure drop (DP) versus dust holding capacity (DHC). This curve can be generated using the ASHRAE test standard mentioned above.

The determination of theoretical energy consumption also must include the time it takes to run a filter from first installation to the moment it is changed out, and this estimate of time coupled with the rate of change of the pressure drop from the DP versus DHC curve can then be used along with HVAC system efficiency and other information to determine a total amount of energy required to operate the HVAC system with that air filter over time.

While the energy required to operate an air filter over the lifetime of that air filter will undoubtedly be one factor to be considered in almost any evaluation, the other factors to be included can vary depending upon the needs of a particular user. Several likely factors are discussed below.

One such factor is the carbon footprint. Numerous governments are beginning to take notice of the carbon footprint created by operation of a particular building, industry, or the like. This carbon footprint can result in cost to the business if too large, or savings to the business if less than a particular standard. Thus, the carbon footprint can lead to direct economic consequences to the user of the HVAC system. The carbon footprint, or $CO_2$ that is generated due to the operation of the filter, can be calculated by multiplying the energy consumed, which has already been determined as above, by a factor established by the Environmental Protection Agency (EPA). Thus, in accordance with the present invention, the system is preferably programmed to carry out this calculation, and to either store or obtain the EPA factor as the case may be. The system could in one embodiment store one or more default values, or even a map associated with the default values to allow a user to find a good default value for a particular location. Alternatively, the system may store a link to such information, for example to an on-line map with associated factors.

The carbon footprint can also be evaluated and presented to the filter user as an estimate of the change in carbon footprint which will occur when switching to a proposed filter as an output. Thus, in addition to economic consequences of a change, the user can also evaluate environmental consequences.

Another clear point of interest would be the total estimated cost due to air filtration, and this cost can be estimated by determining the estimated cost of energy consumed during operation of the filter which is determined above. This calculation can be obtained by multiplying the amount of energy that the filter or filters will consume during its change out cycle by the cost of energy. The cost of energy can be stored by the system in accordance with the present invention, or the system can be programmed to obtain this cost based upon geographic location and the like. Once the cost is determined, it can be annualized, as should be all other costs, so that costs for various different sets of circumstances can be compared on a per year basis.

An estimation can also be conducted as to the cost of all filtration cycle related direct or indirect costs that the user of the system wants to consider and add to the analysis. These types of costs can include the cost of the filter, the cost of changing out the filter, filter disposal costs, loss of production during change out of the filter, purchasing process costs and the like. These costs also should be annualized so that they can be combined with other costs and used to generate a final annual cost of the filter that can be compared to the costs of other filters in the process of determining which filter has the best total value.

Another factor or series of factors that can be included are estimated costs of all annual peripherally related costs that the customer or user wants to include, such as filter storage costs, carbon footprint costs or benefits and the like.

According to the invention, when the process is implemented on a computing device, an interface is ideally presented to the user which will lead the user through a series of data entry steps to determine relevant information and which factors to consider in estimating the final data. This interface can be generated by the computing system onto which the process machine instructions are loaded, and various software on that machine can be utilized to generate the appropriate display. The actual machine operating instructions for generating the display are those which would be well-known to a person skilled in the art to which this invention is related, and the actual operating system of the computing device does not form any part of the present invention.

FIG. 1 schematically shows a series of steps each leading to an output which is then combined to determine a total estimated operating cost of a particular filter. According to the invention, this calculation can be carried out for two or more different filters to generate an estimated operating cost for each of the filters, and these numbers can then be compared to determine which filter is most economical in that particular set of circumstances. The process of the present invention when loaded onto a computing device can advantageously be adapted to present the resulting calculated total operating costs and related information in any meaningful form to help the user compare the differences in total operating costs and the like. One way to compare these estimations would be to carry out the steps of FIG. 1 for the existing filter of a particular user, and then to carry out these calculations for the proposed filter, of course using the DP versus DHC curve of that proposed filter, and carrying out the calculation to the point on that curve where DHC for the proposed filter is equal to DHC of the current filter at change out. The total cost calculation of the proposed filter can then be subtracted from the total cost calculation of the existing filter to determine a total cost change that would result from using the proposed filter, and this information can be presented to the user of the system.

Additional examples of cost information that a user can be prompted to enter include work or school absenteeism caused by inappropriate air filtration. Use of a higher efficiency filter that consumes more energy but that produces cleaner air and in turn reduces the absenteeism in schools and improves the education efficiency can lower cost of teaching and providing a better education, and in a business can increase the overall productivity. Thus, a user of the system could enter estimates of this information as well, which can be factored into the overall cost estimates of current and proposed air filters in order to provide a comprehensive cost comparison.

The system and process of the present invention can also be utilized to determine the optimum proposed filter change out time for a particular filter. This can be done on its own as a useful determination or can be done in combination with the above calculations to first determine the impact of switching to a proposed filter operated for the same duration as the current filter, and then to optimize the change out point of the proposed filter. Thus, according to the invention, a first run can be done to determine if savings can be obtained by changing to a proposed filter while operating the proposed filter for the same amount of time as the current filter, a second run can then be made to determine when that proposed filter should be changed out to further enhance efficiency and reduce estimated total operating costs. A different change out cycle, that is, earlier or later than when the user normally changes out filters, is of course, a useful estimate to provide. The system and method can also be used to evaluate estimated economic and/or carbon footprint impact of changing out at other pressure drops.

It should be appreciated that although atmospheric conditions are not constant, when comparing two filters the relative performance of the filters with respect to each other are very good indicators since both filter estimates are based on the same atmospheric conditions which is a reasonable assumption for the same premises.

The ASHRAE standard 52.2 is useful for generating various different information and parameters for a particular filter. Attached as Appendix A is a sample test report following the ASHRAE standards, for a particular filter. This shows the test results for the filter as carried out by an independent testing laboratory, and the data set forth in this report can be provided to or otherwise stored by the system in accordance with the present invention, preferably for a series of different filters, and used in combination with the actual on-site or experience information collected from a customer, to make the calculations and determinations which are to be made according to the invention. Another standard which could be used is as EN771, and similar standards could likewise be used.

Turning now to FIGS. 2-5, a series of illustrations of data collection and output screens which can be generated in accordance with the present invention are shown.

Figure 2:

FIG. 2 shows a data collection screen wherein the various different contact information for a particular HVAC operator can be collected, followed by a section in this illustration identified as "customer filtration system" wherein information specific to the particular filter user location and operating practice can be collected. In this section, the time of operation, average change-out cycle, number of filters in a system, system efficiency, local $CO_2$ emissions, local energy costs and various other aspects of the actual system are collected so that the calculations to be made can be based upon the actual system in question.

Also collected at this time is information related to the current filter used by the HVAC operator, and various information related to this filter such as the average pressure drop of the filter when changed, cost of each filter, etc. Also shown on this screen is a column for collecting information related to the filter to be proposed to the HVAC operator.

In the example illustrated in the figures shown, it can be seen that the current filter is a Riga-Flo Camfil-Farr M14 12" B G BH filter. This filter would hopefully be found within the existing data base of the system, and if not, then some additional specific information would need to be obtained from the filter user or some other source, or from an independent test laboratory. In this instance, the filter is in the database and filter characteristics are shown in the screen.

Figure 3:
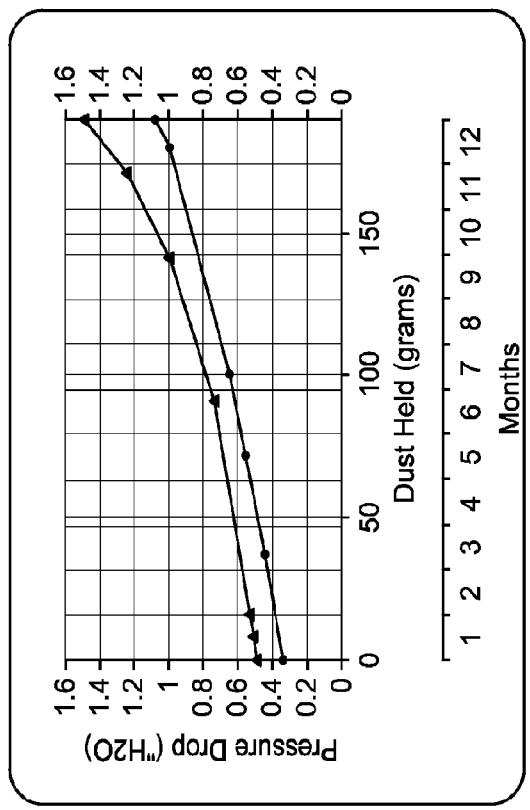

Also collected on this screen, or entered on this screen, is an identification of the filter to be proposed as an improvement. The choice of proposed filter is made from a list of filters stored in or accessible to the system library, and information similar to that shown and described in the above test report is preferably available for each filter option. By entering the name of a proposed filter, relevant details are brought to bear by the system and considered in making a final determination. In the example of FIG. 2, the proposed filter is a Legacy CLC M14 12" 9.5 m² H S CLC filter Once this information is entered, the first step is to calculate what savings based upon energy costs, filter replacement costs and any other source of costs considered in the initial entry of data are experienced. Upon considering all these costs, an initial determination can be made as to whether the proposed filter type would result in a savings. FIG. 3 shows a typical outcome from this step, showing in table and graph form the cost for operating the existing filter as compared to the cost for operating the proposed filter. It is noted that in this instance the proposed filter has a better efficiency than the existing filter, and therefore the proposed filter can be changed-out on the same timetable as the original filter, but after having reached a fraction of the pressure drop reached by the existing filter.

Figure 4:
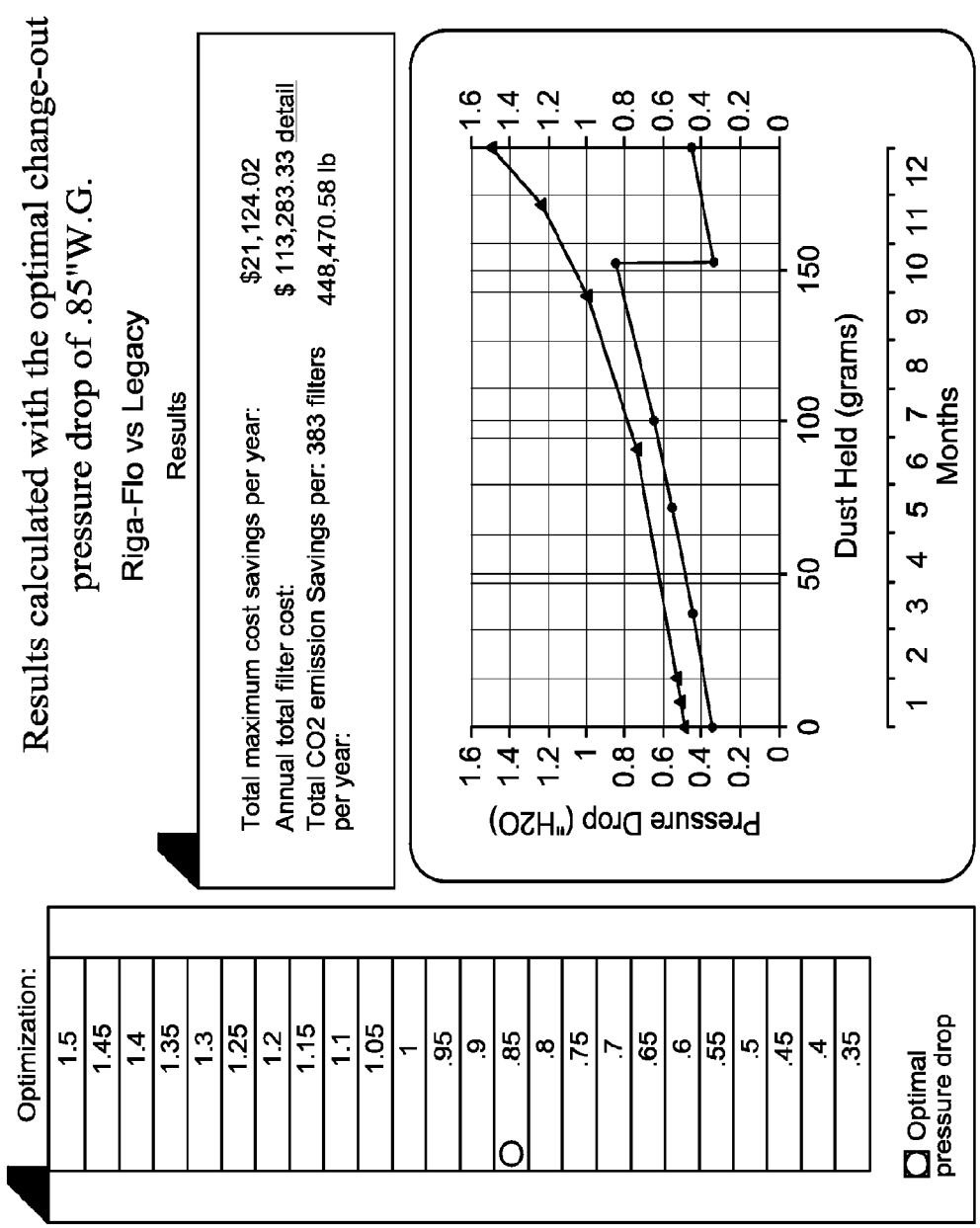

Once it is established that the new filter type appears to be an improvement over the original filter, the next step is to take the same entered information and use the optimize option as shown in FIG. 2, and this results in an optimization of the new filter type to determine when the filter should be changed-out. This is illustrated in FIG. 4. In this way, the ideal or optimal time for changing-out the proposed new filter can also be determined. In this particular instance, the old filter had been changed-out at twelve months. In the test data, it is shown that while the existing filter reaches the pressure drop of 1.5" of water over the relevant time frame, the proposed filter has a much flatter curve of dust held (in grams) to the pressure drop (in inches of water). This output can include a graph of pressure drop versus time and/or dust held for each filter, to further highlight the advantages to be gained by utilizing the proposed filter. Finally, from the presentation screen of FIG. 2, once all data has been entered and the filter optimized, a report can be generated at the optimal pressure drop to change-out the proposed new filter, and this report can summarize the comparison of the old filter type with the new filter type under the same operating parameters, and further with the new filter type under the optimized operating parameters. A sample report is produced in FIGS. 5a-5d. In this way, a potential customer or purchaser of the filters using the system and method of the invention can determine which filter and way to operate the filter would be most advantageous for that particular customer's system and practices in operating the system.

FIG. 5a shows a summary in table form comparing the cost of the current filter with the estimated cost of the proposed filter operated at the same change-out cycle and also at the optimized change-out cycle.

FIG. 5b shows a more detailed breakdown of the summary of FIG. 5a, including information both a yearly and cyclical basis.

FIG. 5c summarizes the information used by the system and method for making the relevant estimates, and FIG. 5d is a summary of information presented to the user to more fully complete the information presented.

It should be noted that while the above example shows use of the system purely for the purpose of determining whether a proposed filter is better, and by how much, this system could likewise be used by a seller of filters to determine the price at which a proposed filter could be sold and still be attractive to the consumer. In order to do this, the above steps could be made while changing the proposed price for the proposed filter and thereby gaining more knowledge as to the economic impact upon the actual consumer based upon each possible proposed price.

The above illustrates one example of the information to be collected and one way of displaying the results from the system and method of the present invention through which a user of the system can be presented with an efficient presentation of the relevant determinations.

Figure 6:
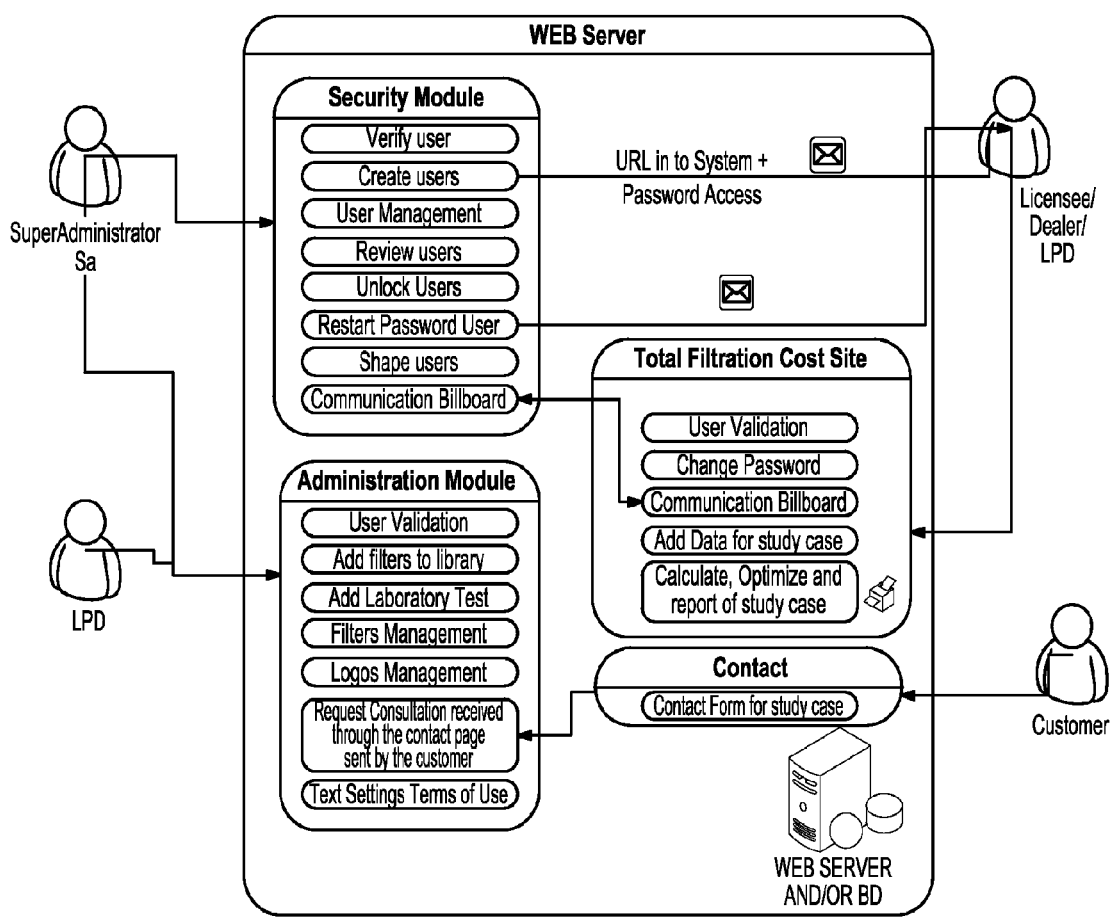
FIGS. 6-7 show system configurations and modules according to the invention.
Figure 7:
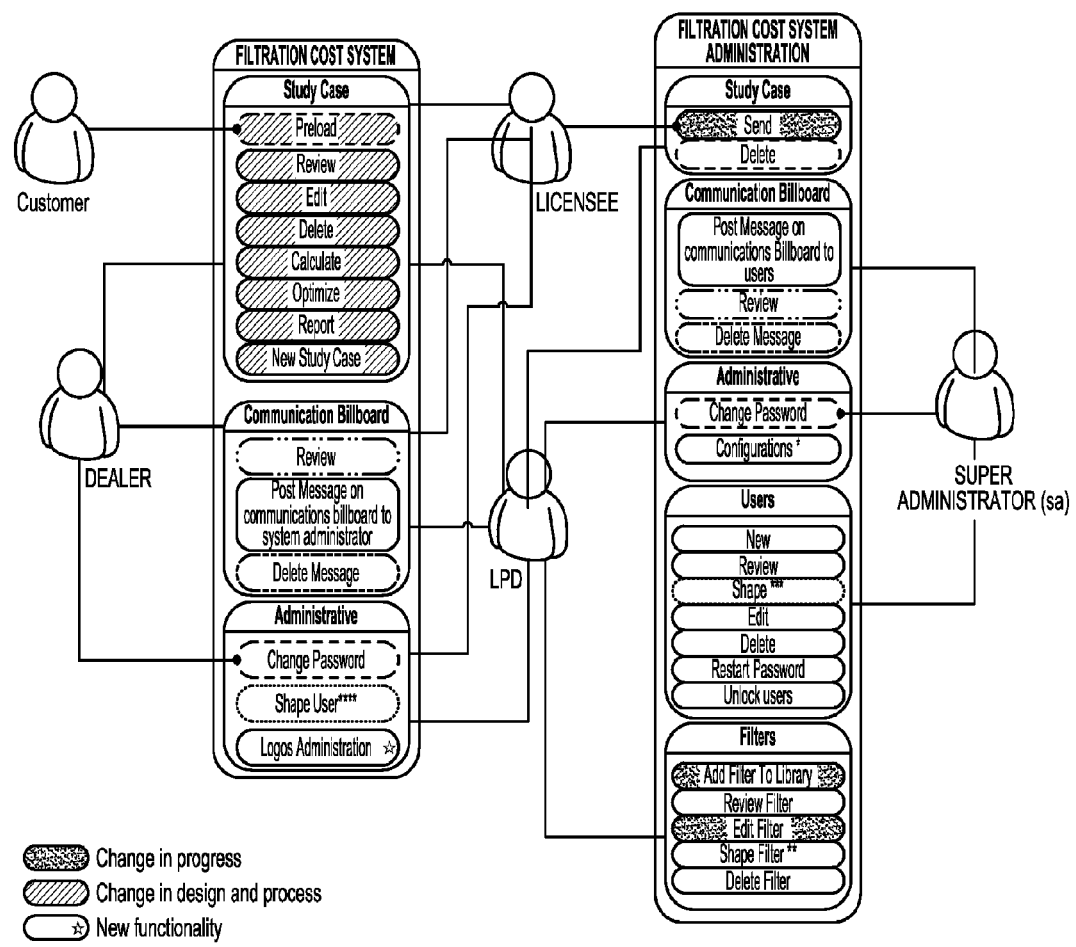

FIGS. 6 and 7 further illustrate the flow of operation of various different components of the present invention. FIG. 6 shows a general flow in connection with a security module, an administration module, a total filtration cost site, and the contact point with a consumer.

At the security module, a super-administrator or SA can conduct various high-level configurations of the system, such as verifying and creating users, and the like.

An administration module is also shown, and this can be modified by an authorized user downstream, for example, in order to validate users, add filters to the libraries, add laboratory testing, manage filters in the local data base, manage logos of various different licensed dealers who will be using the system, and the like.

There is a total filtration cost site or module, typically to be operated by a licensee such as a dealer or the like, and at this site once all passwords have been cleared, the licensee can enter data as collected from the customer. The total filtration cost site communicates with the security module, and then typically utilizes entered data to calculate relevant information using the server-based system to perform some or all operations. The result is a calculation, optimization and report of results as shown above in connection with FIGS. 2-5. These results can be presented to the licensee or dealer, or can be presented directly to the customer.

It is also noted that FIG. 6 shows a communication billboard which goes between a licensee in charge of the total filtration cost site and the security module. This communication billboard can be utilized to conduct general communications between super-administrator level people and the customers, for the purposes of system support, trouble shooting and feedback and the like.

It is also noted that a customer desiring to obtain consultation according to the present invention could enter contact information with the administration module, which will result in a consultant contacting the consumer to work through the functioning of the total filtration cost site as discussed above.

FIG. 7 illustrates a further series of different functionality which is presented to each different type of user and of course with the present invention. Thus, this figure illustrates a filtration cost system, and this system includes a series of steps for studying the case, a communication billboard and an administrative function.

The customer operating a system as illustrated in FIG. 7 could begin operation of the filtration cost system through pre-loading of specific data, which is specific to the location at which the filter is to be used.

FIG. 7 shows the various different personnel potentially involved in the use of the system, as well as connection points to various different modules to show what that particular individual's role would be in operating the system according to the present invention.

FIGS. 8-11 are directed to an embodiment of the invention wherein provision is made for users of systems having more than one stage. The program according to the invention is preferably configured to handle up to five stages, as this is as many stages as are used in typical multi-stage systems. In such systems, each stage has a filter, and the configuration of the system usually is such that the filter for a second or subsequent stage cannot be changed without accessing and removing the earlier stage filter(s). Since it does not make sense to remove an earlier stage filter to replace a later stage filter, and then reinstall the partially used earlier stage filter, it is the most effective use of filters to select and filters and operate the system such that the later stage filter is to be changed at the same cycle, or in multiples of cycles, of the earlier stage filter.

Thus, according to the invention, the information gathering stage for this embodiment, as illustrated by FIGS. 8 and 9, would start with a screen for a first stage and then have a screen for each subsequent stage for collecting relevant information concerning the filter in each stage. With this information, the system is programmed to select filters which can operate in the various stages and be changed out as desired, with later filters being changed on cycle, or in multiples of the cycle, of the earlier filters.

Figure 11:
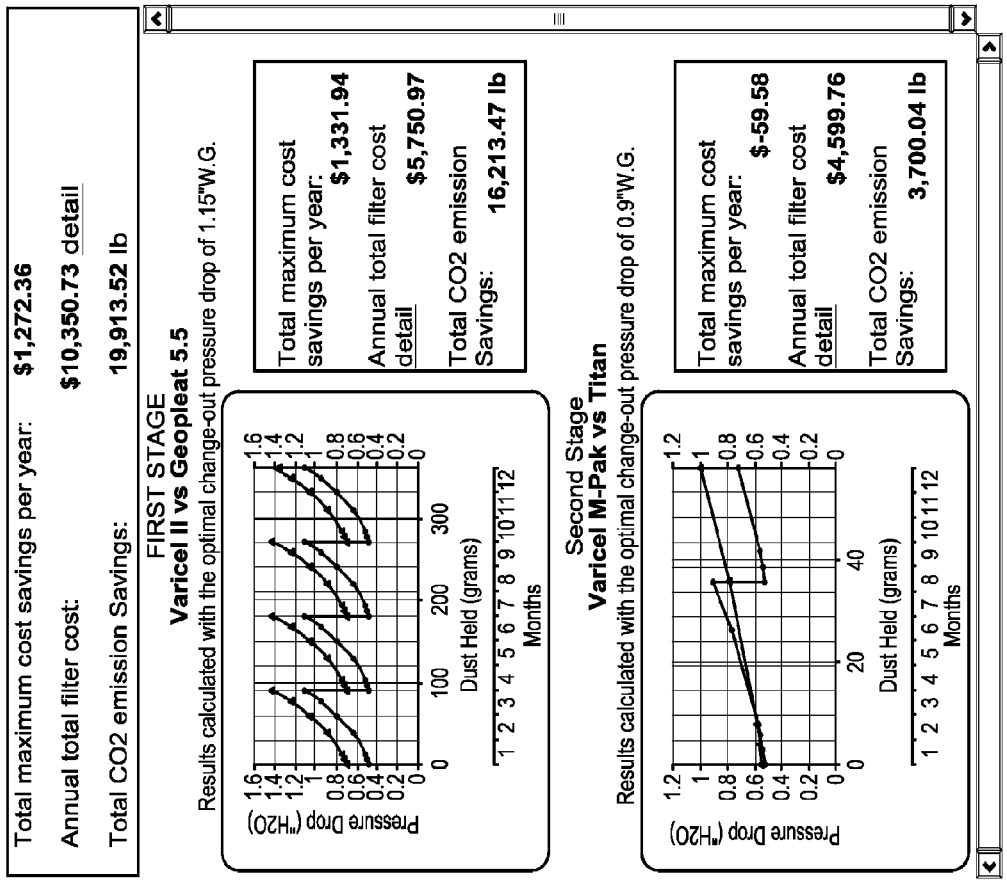

Thus, for example, FIG. 8 shows information entered relative to a first stage of a two stage system. FIG. 8 shows that the filters for the first stage are changed out on a 3 month cycle. FIG. 9 shows the second stage of this system, and shows that the filters for this stage are changed on a 12 month cycle. This aspect of the present invention advantageously allows the system to evaluate different filters and/or filter change out cycles for the first and second stages and FIGS. 10 and 11 show an output screen for this determination wherein it is determined (FIG. 10) that substantial savings can be accomplished with proposed filters and continuing to change the stage 1 filters on a 3 month cycle while changing the second stage filters on a 12 month cycle. In FIG. 11, results of optimization are shown. The system has optimized change our cycles for the first stage to be at a pressure drop of 1.15 inches w.g. and for the second stage at a pressure drop of 0.9 inches w.g. This can then be modified to take into account the advantage of changing the second stage filters on cycle with the first stage filters as discussed above.

It should be understood that the illustrations provided in FIGS. 2-11 above show samples of how the system and method according to the invention can be used by specific individuals such as administrators, dealers, licensees and customers to obtain and/or provide useful information. These illustrations are by way of example, and it is of course understood that other presentations could be made by methods and systems operating according to the method and still be well within the scope of the present invention.

We claim:

1. A method for estimating energy use in an air filtration system using a preselected air filter, comprising the steps of:
   entering filtration system information into a computer having access to dust holding capacity versus pressure drop curves for a plurality of different air filters, wherein the filtration system information includes user experience information including change out time for a current air filter in the system;
   determining an estimated current energy use of the air filtration system for the current air filter in the system using the user experience information and the dust holding capacity versus pressure drop curves for the current air filter;
   determining an estimated proposed energy use of the air filtration system for a proposed air filter different from the current air filter using the user experience information and the dust holding capacity versus pressure drop curves for the proposed air filter; and
   presenting a comparison of the estimated energy use for the current air filter and for the proposed air filter on a display of the computer, as well as a proposed schedule for changing the proposed air filter; and
   changing out filters in the air filtration system following the proposed schedule.

2. The method of claim 1, wherein the computer has access to energy cost information, and wherein the presenting step includes presenting estimated cost of use on the display of the computer.

3. The method of claim 2, wherein the filtration system information includes at least one additional cost information selected from the group consisting of filter cost, filter changing cost, used filter disposal cost, carbon footprint cost and combinations thereof, and wherein the estimated cost includes the at least one additional cost.

4. The method of claim 1, wherein the filtration system information includes change out times for the current air filter, and further comprising determining an optimized change out time for the proposed air filter; and presenting the optimized change out time on the display of the computer.

5. The method of claim 4, wherein the computer has access to energy cost information, and wherein the presenting step includes presenting estimated cost of use on the display of the computer.

6. The method of claim 5, wherein the filtration system information includes at least one additional cost information selected from the group consisting of filter cost, filter changing cost, used filter disposal cost, carbon footprint cost and combinations thereof, and wherein the estimated cost includes the at least one additional cost.

7. The method of claim 6, wherein the system has at least two stages each having a current air filter, and wherein the optimizing step includes optimizing the change out cycle of filters from each of the at least two stages.

8. The method of claim 1, wherein the filtration system information includes change out times for the current air filter, and further comprising determining an optimized change out time for the current air filter; and presenting the optimized change out time on the display of the computer.

9. The method of claim 8, further comprising entering information concerning additional proposed air filters, selecting a desired proposed air filter from the additional proposed air filters, and then optimizing change out time for the desired proposed air filter.

10. The method of claim 1, wherein the user experience information includes pressure drop at a start of operation for the current air filter and pressure drop at change out time for the current air filter.

* * * * *